United States Patent
Röder et al.

(10) Patent No.: US 7,906,342 B2
(45) Date of Patent: *Mar. 15, 2011

(54) MONITORING TREATMENT OF CANCER PATIENTS WITH DRUGS TARGETING EGFR PATHWAY USING MASS SPECTROMETRY OF PATIENT SAMPLES

(75) Inventors: Heinrich Röder, Steamboat Springs, CO (US); Maxim Tsypin, Steamboat Springs, CO (US); Julia Grigorieva, Steamboat Springs, CO (US)

(73) Assignee: Biodesix, Inc., Steamboat Springs, CO (US)

( * ) Notice: Subject to any disclaimer, the term of this patent is extended or adjusted under 35 U.S.C. 154(b) by 57 days.

This patent is subject to a terminal disclaimer.

(21) Appl. No.: 12/584,594

(22) Filed: Sep. 8, 2009

(65) Prior Publication Data

US 2010/0055100 A1  Mar. 4, 2010

Related U.S. Application Data

(63) Continuation-in-part of application No. 11/396,328, filed on Mar. 31, 2006, now Pat. No. 7,736,905, and a continuation-in-part of application No. 12/321,392, filed on Jan. 20, 2009, now Pat. No. 7,858,389, and a continuation-in-part of application No. 12/321,393, filed on Jan. 20, 2009, and a continuation-in-part of application No. 12/321,394, filed on Jan. 20, 2009, now Pat. No. 7,858,390.

(60) Provisional application No. 61/191,927, filed on Sep. 12, 2008.

(51) Int. Cl.
*G01N 24/00* (2006.01)

(52) U.S. Cl. ............ 436/173; 436/86; 436/171; 435/6; 435/69.9; 435/372; 702/20; 702/179

(58) Field of Classification Search .................. None
See application file for complete search history.

(56) References Cited

U.S. PATENT DOCUMENTS 7,736,905 B2  6/2010  Roder et al. ............... 436/173

(Continued)

FOREIGN PATENT DOCUMENTS

WO  WO 2004/012588  2/2004

(Continued)

OTHER PUBLICATIONS

Extended European Search Report dated Aug. 25, 2010 in European Application No. 10003343.0.

(Continued)

*Primary Examiner* — Yelena G Gakh
*Assistant Examiner* — Robert Xu
(74) *Attorney, Agent, or Firm* — McDonnell Boehnen Hulbert & Berghoff LLP

(57) ABSTRACT

Methods using mass spectral data analysis and a classification algorithm provide an ability to determine whether a non-small-cell lung cancer patient, head and neck squamous cell carcinoma or colorectal cancer patient has likely developed a non-responsiveness to treatment with a drug targeting an epidermal growth factor receptor pathway. As the methods of this disclosure require only simple blood samples, the methods enable a fast and non-intrusive way of measuring when drugs targeting the EGFR pathway cease to be effective in certain patients. This discovery represents the first known example of true personalized selection of these types of cancer patients for treatment using these classes of drugs not only initially, but during the course of treatment.

3 Claims, 3 Drawing Sheets

U.S. PATENT DOCUMENTS

| | | | |
|---|---|---|---|
| 2005/0048547 A1 | 3/2005 | Zhao et al. | 435/6 |
| 2005/0164218 A1 | 7/2005 | Agus et al. | 435/6 |
| 2005/0267689 A1 | 12/2005 | Tsypin | 702/19 |
| 2006/0029574 A1 | 2/2006 | Albitar et al. | 424/93.1 |
| 2007/0231921 A1 | 10/2007 | Röder et al. | 436/173 |

FOREIGN PATENT DOCUMENTS

| | | |
|---|---|---|
| WO | WO 2005/010492 | 2/2005 |
| WO | WO 2005/098445 | 10/2005 |

OTHER PUBLICATIONS

Reyzer et al. *MALDI mass spectrometry for direct tissue analysis: a new tool for biomarker discovery*, Journal of Proteome Research vol. 4, No. 4, pp. 1138-1142 (2005).

Yanagisawa et al. *Proteomic patterns of tumour subsets in non-small-cell lung cancer*, The Lancet, vol. 362, pp. 433-439 (Aug. 9, 2003).

Extended European Search Report in EP 07754043.3, dated Aug. 6, 2009.

Bhanot et al., *A Robust Meta-Classification Strategy for Cancer Detection from MS Data*, Proteomics, vol. 6, pp. 592-604 (2006).

Metro, et al., "Epidermal Growth Factor Receptor (EGFR) Targeted Therapies in Non-Small Cell Lung Cancer (NSCLC)", Reviews on Recent Clinical Trials, vol. 1, No. 1, pp. 1-13 (2006).

Taguchi, et al., "Mass Spectrometry to Classify Non-Small-Cell Lung Cancer Patients for Clinical Outcome after Treatment with Epidermal Growth Factor Receptor Tyrosine Kinase Inhibitors: A Multicohort Cross-Institutional Study", Journal of the National Cancer Institute, vol. 99, Issue 11, pp. 838-846 (2007).

Ladanyi, et al., "Lung adenocarcinoma: guiding EGFR-targeted therapy and beyond", Modern Pathology, vol. 21, pp. S16-S22 (2008).

Engelman et al. *Mechanisms of Acquired Resistance to Epidermal Growth Factor Receptor Tyrosine Kinase Inhibitors in Non-Small Cell Lung Cancer*, Clin. Cancer Res. 2008; 14(10) pp. 2895-2899 (May 15, 2008).

Lynch et al., *Activating Mutations in the Epiderman Growth Factor Receptor Underlying Responsiveness of Non-Small-Call lung Cancer to Getfitinib*, The New England Journal of Medicine, May 20, 2004, vol. 350, No. 21, pp. 2129-2139 (2004).

Howard et al. *Identification and validation of a potential lung cancer serum biomarker detected by matrix-assisted laser desorption/ionization-time of flight spectra analysis*, Proteomics vol. 3, pp. 1720-1724 (2003).

D. Coomans and D.L. Massart, *Alternative k-Nearest Neighbour Rules in Supervised Pattern Recognition*, Part 1, Analytica Chimica Acta, 136, pp. 15-27 (1982).

Office Action in EP application No. 07754043.3 dated Sep. 14, 2010.

Bhanot et al. *A robust meta-classification strategy for cancer detection from MS data Proteomics*, vol. 6, NR 2, pp. 592-607 (Jan. 2006).

U.S. Appl. No. 12/661,129, filed Mar. 10, 2010, Roder et al.
U.S. Appl. No. 12/661,124, filed Mar. 10, 2010, Roder et al.
U.S. Appl. No. 12/321,394, filed Jan. 20, 2009, Roder et al.
U.S. Appl. No. 12/321,393, filed Jan. 20, 2009, Roder et al.
U.S. Appl. No. 12/321,392, filed Jan. 20, 2009, Roder et al.

MONITORING TREATMENT OF CANCER PATIENTS WITH DRUGS TARGETING EGFR PATHWAY USING MASS SPECTROMETRY OF PATIENT SAMPLES

CROSS-REFERENCE TO RELATED APPLICATIONS

This application is a continuation-in-part of our prior U.S. Patent Application Ser. No. 11/396,328 filed Mar. 31, 2006, currently pending, published as U.S. Patent Publication No. 2007/0231921. The entire content of the '121 patent application publication is incorporated by reference herein.

This application also claims priority benefit to U.S. Provisional Application Ser. No. 61/191,927 filed on Sep. 12, 2008, which is also incorporated by reference herein.

This application is also a continuation in part of U.S. Patent Application Ser. Nos. 12/321,392, 12/321,393 and 12/321,394, each filed on Jan. 20, 2009, the content of each of which is incorporated by reference herein.

BACKGROUND

This invention relates to the field of monitoring of treatment of cancer patients with drugs targeting the epidermal growth factor receptor (EGFR) pathway. The monitoring involves mass spectral analysis of blood samples from the patient in conjunction with a classification algorithm using a training set of class-labeled spectra from other patients with the disease.

Non-Small-Cell Lung Cancer (NSCLC) is a leading cause of death from cancer in both men and women in the United States. There are at least four (4) distinct types of NSCLC, including adenocarcinoma, squamous cell, large cell, and bronchoalveolar carcinoma. Squamous cell (epidermoid) carcinoma of the lung is a microscopic type of cancer most frequently related to smoking. Adenocarcinoma of the lung accounts for over 50% of all lung cancer cases in the U.S. This cancer is more common in women and is still the most frequent type seen in non-smokers. Large cell carcinoma, especially those with neuroendocrine features, is commonly associated with spread of tumors to the brain. When NSCLC enters the blood stream, it can spread to distant sites such as the liver, bones, brain, and other places in the lung.

Treatment of NSCLC has been relatively poor over the years. Chemotherapy, the mainstay treatment of advanced cancers, is only marginally effective, with the exception of localized cancers. While surgery is the most potentially curative therapeutic option for NSCLC, it is not always possible depending on the stage of the cancer.

Recent approaches for developing anti-cancer drugs to treat the NSCLC patient focus on reducing or eliminating the ability for cancer cells to grow and divide. These anti-cancer drugs are used to disrupt the signals to the cells to tell them whether to grow or die. Normally, cell growth is tightly controlled by the signals that the cells receive. In cancer, however, this signaling goes wrong and the cells continue to grow and divide in an uncontrollable fashion, thereby forming a tumor. One of these signaling pathways begins when a chemical in the body, called epidermal growth factor, binds to a receptor that is found on the surface of many cells in the body. The receptor, known as the epidermal growth factor receptor (EGFR) sends signals to the cells, through the activation of an enzyme called tyrosine kinase (TK) that is found within the cells. The signals are used to notify cells to grow and divide.

The use of targeted therapies in oncology has opened new opportunities to improve treatment options in advanced stage solid tumors where chemotherapy was previously the only viable option. For example, drugs targeting the epidermal growth factor receptor (EGFR) pathway (including without limitation, Tarceva (erlotinib), Erbitux (cetuximab), Iressa (gefitinib)) have been approved or are in evaluation for treatment of advanced stage solid tumors in particular non-small cell lung cancer (NSCLC). Metro G et al, Rev Recent Clin Trials. 2006 January;1(1):1-13.

While in some trials EGFR-Inhibitors (EGFR-I) such as those mentioned above have been shown to generate sufficient survival benefit even in unselected populations, in others there was no substantial benefit. This lead AstraZeneca to withdraw their EGFR-tyrosine kinase inhibitor (TKI) (gefitinib, Iressa) from the United States market. Even in the case of approved EGFR-Is it has become more and more clear that efficient and reliable tests are necessary to identify those patients that might benefit from treatment with EGFR-Is vs. those that are not likely to benefit. Ladanyi M, et al., Mod Pathol. 2008 May; 21 Suppl 2:S16-22.

In our U.S. patent application Ser. No. 11/396,328 we have shown that a simple serum-based pre-treatment test using mass spectrometry and sophisticated data analysis techniques using a classifier and a training set of class-labeled spectra from other patients with the disease can be used for patient selection for treatment with drugs targeting the EGFR pathway in non-small cell lung cancer patients. See also Taguchi F. et al, JNCI-2007 v99(11), 838-846. The test, called VeriStrat in its commercial version, assigns the label "VeriStrat good" or "VeriStrat poor" to pre-treatment serum or plasma samples. It has been shown in the JNCI paper that "VeriStrat good" patients are more likely to benefit from EGFR-I treatment than VeriStrat poor patients with a hazard ratio of "VeriStrat good" vs. "VeriStrat poor" patients of approximately 0.5.

There is increasing evidence that the tumors of some patients develop resistance to EGFR inhibitors (EGFR-Is) during treatment, even if the treatment was initially successful as measured by RECIST response criteria. Engelman J A, et al. Clin Cancer Res. 2008 May 15;14(10):2895-9. It is unfortunate that currently the only quantitative way to assess tumor growth is by imaging techniques like x-rays or more preferably CT imaging. These are typically scheduled at least one month apart, lead to increases in cumulative radiation dose, and require hospitals visits. Also there is at least some doubt about the correlation of tumor growth measured by CT and eventual outcome measured by overall survival.

SUMMARY OF THE INVENTION

We have discovered that the methods of mass spectral analysis of patient samples and classification using a training set described in our prior patent application provide not only a selection tool for initially identifying patients as being likely to benefit from drugs targeting the EGFR pathway, but also that it is possible to correlate changes in the classification label for a patient's samples over time with the occurrence of disease progression. As the methods of this disclosure require only simple blood samples, the methods enable a fast and non-intrusive way of measuring when drugs targeting the EGFR pathway cease to be effective in certain patients during the course of treatment. This discovery represents the first known example of true personalized selection of NSCLC patients for treatment using these classes of drugs not only initially, but during the course of the treatment.

We have further discovered that the methods of this disclosure also are effective for personalized selection of other kinds of cancer patients for treatment using drugs targeting the EGFR pathway initially and during the course of the treatment. Specifically, the methods of this disclosure are effective for monitoring treatment for head and neck squamous cell carcinoma (HNSCC) and colorectal cancer (CRC) patients.

In one specific embodiment, a method is disclosed of determining whether a NSCLC, HNSCC or CRC patient has developed non-responsiveness to treatment with a drug targeting the EGFR pathway (e.g, an EGFR-I such Tarceva (erlotinib), Erbitux (cetuximab), Iressa (gefitinib), or equivalent) comprising the steps of:

a) obtaining a mass spectrum from a blood-based sample from the patient;

b) performing one or more predefined pre-processing steps on the mass spectrum obtained in step a);

c) obtaining integrated intensity values of selected features in said spectrum at one or more predefined m/z ranges after the pre-processing steps on the mass spectrum in step b) have been performed;

d) using the values obtained in step c) in a classification algorithm using a training set comprising class-labeled spectra produced from blood-based samples from other patients to identify the patient as having developed a non-responsiveness to treatment with the said drug.

The method and steps a)-d) are preferably performed periodically over the course of treatment, e.g., every 30 or 60 days.

Method steps b), c) and d) can be implemented in a general purpose computer programmed to perform the one or more predefined pre-processing steps (e.g., background subtraction, spectral alignment and normalization), the obtaining of the integrated intensity values of selected features in the spectrum, and the application of the classification algorithm to the obtained values using the training set of class-labeled spectra (e.g., using a k-nearest neighbor classification algorithm).

In another aspect, a method is disclosed of facilitating treatment of a NSCLC, HNSCC or CRC patient patient, comprising the steps of:

1) assigning a baseline class label for the patient using a classifier operating on integrated intensity values at pre-defined m/z ranges in mass-spectral data obtained from a blood-based sample of the patient and a training set comprising class-labeled spectra from other patients, the baseline class label indicating whether the patient is likely to benefit from administration of a drug targeting an epidermal growth factor receptor pathway. If the baseline class label is "good" (or the equivalent), the patient would be likely to benefit and the drug is administered to the patient; and 2) thereafter, while the patient is being treated with the drug, a) obtaining a mass spectrum of a blood-based sample of the patient, b) performing one or more predefined pre-processing steps on the mass spectrum, c) obtaining integrated intensity values of selected features in said spectrum at one or more predefined m/z ranges after the pre-processing steps on the mass spectrum have been performed, and d) assigning a further class label for the sample using the classifier and the training set, the further class label indicating whether the patient has developed a non-responsiveness to the treatment with the said drug. This step 2) is preferably performed periodically over the course of treatment, e.g., every 30 or 60 days.

Method steps 1) and 2) can be computer-implemented by a general purpose computer that is programmed to receive mass spectral data from the blood-based sample of the patient, stores the training set data, and is programmed to perform the predefined pre-processing steps, the obtaining of the integrated intensity values of selected features in the spectrum and conduct the classification algorithm on the sample and the training set, e.g., using a k-nearest neighbor classification algorithm to thereby assign a further class label to the sample.

The methods of this disclosure can be performed by a service provider that receives blood-based samples, generates the initial class label and the further class label, and then provides the initial and further class labels to requesting hospital, clinic or physician treating the patient.

DETAILED DESCRIPTION

Figure 1:
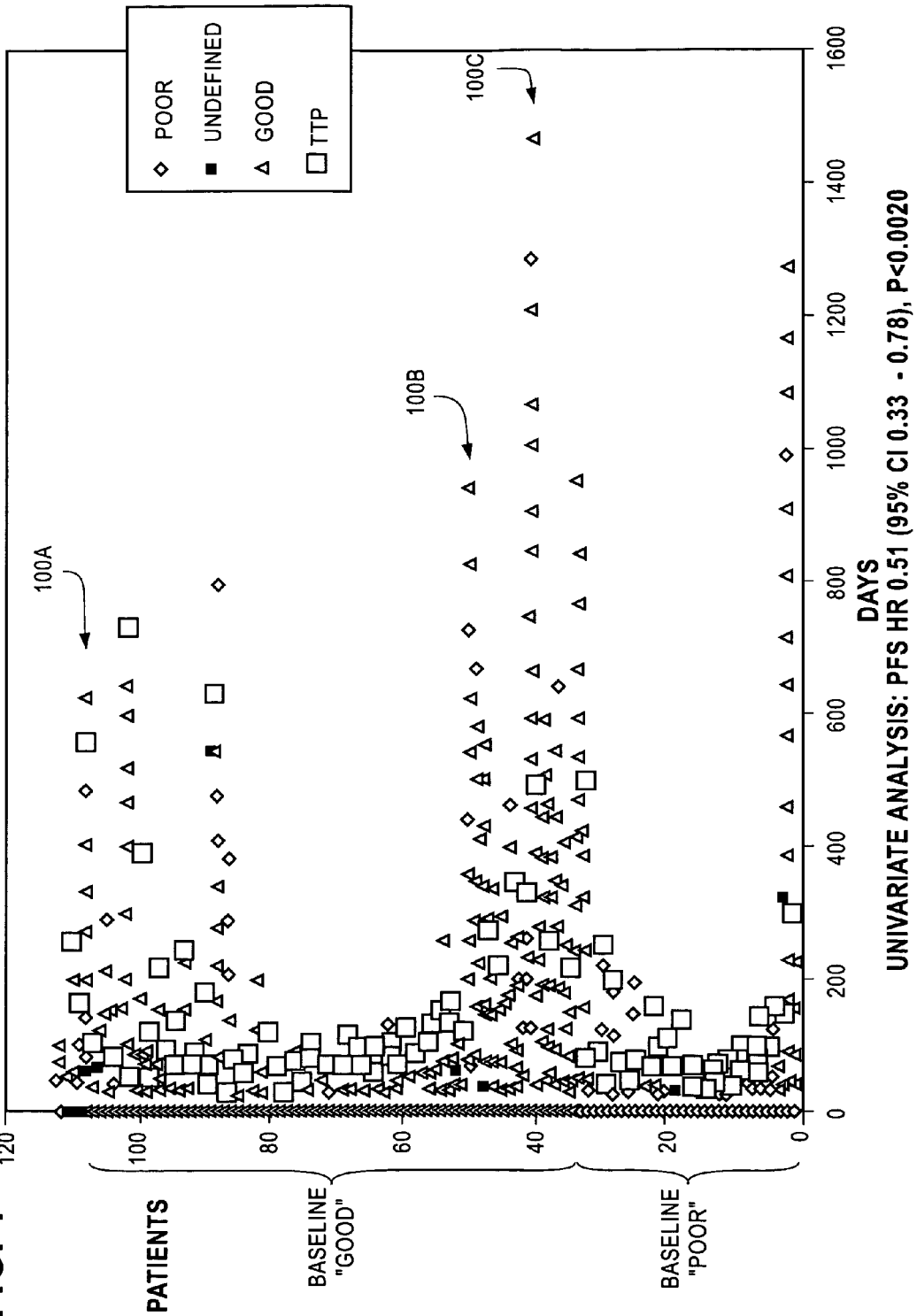
FIG. 1 is a graph plotting the changes in classification labels for 111 NSCLC patients (arranged along the vertical axis) at different times, with time plotted in days along the horizontal axis. The time to progression ("TTP") of the disease for each of the patients is indicated by the square symbol.

This disclosure will describe an example of methods for patient selection for drugs targeting the EGFR pathway during the course of treatment wherein the patient is a NSCLC patient. We have discovered that the methods are equally applicable to CRC and HNSCC cancer patients as well.

In order to follow changes in the class labels assigned to a patient during the course of treatment using the above-described classification methods described in our prior patent application U.S. 2007/0231921, one needs blood-based samples from the patient taken before treatment, and at reasonable intervals during treatment, e.g., every 30 days, 60 days or 100 days. In the study described below, these samples were available on a subset of the samples used in the Taguchi et al. publication. For 111 patients serum was collected at baseline, after one month of therapy, and afterwards every two months until progression or death.

The population characteristics of these samples are shown in Table 1. At progression we had 109 complete sets of patients attributes (attributes were not available for two patients). All patients were treated with the EGFR-TKI gefitinib monotherapy following the baseline serum collection. The median time-to-progression was 3.4 months and the median overall survival (from baseline) was 8.3 months. Two patients were still alive at the close of the study.

TABLE 1

Summary population characteristics for the patients used in this study

| Variable | Value |
|---|---|
| Total enrolled | 111 |
| Median age (range), years | 68 (36-90) |
| Sex (male/female) | 86 (77%)/25 (23%) |
| Smoking history (ever vs never-smokers) | 88 (84%)/17 (16%) |
| PS 0/1/2 | 46 (41%)/46 (41%)/19 (18%) |

TABLE 1-continued

Summary population characteristics for the patients used in this study

| | Value |
|---|---|
| Histological classification | |
| Adenocarcinoma | 55 (50%) |
| NSCLC | 23 (21%) |
| Squamous cell carcinoma | 26 (23%) |
| BAL | 7 (6%) |
| TNM classification | |
| Stage IB/IIB/IIIA | 5 (5%) |
| Stage IIIB | 14 (13%) |
| Stage IV | 92 (82%) |
| Median months on treatment (range) | 3.5 (0.7-47) |

Methods

Mass spectra were generated at Hospitale San Raffaele following the procedure described in our prior patent application patent publication No. 2007/0239121. Upon receipt of these spectra we analyzed them using the pre-processing, feature extraction, and classifier using K-nearest neighbor classification algorithm and the training set as described in our prior patent application. These methods are set forth in detail in U.S. Patent Publication No. 2007/0231921, which is incorporated by reference herein, and therefore a detailed explanation is not set forth for the sake of brevity. The methods are summarized below.

The resulting labels generated by the classifier ("good", "poor" and "undefined") were correlated with time-to-progression and overall survival data using standard statistical methods using GraphPad Prism software (GraphPad Software, La Jolla Calif.). In this discussion, a class label of a serum sample which is classified by the classifier as "good" indicates that a patient is likely to continue to benefit from treatment with drugs targeting the EGFR pathway, whereas a class label of a serum sample which is classified by the classifier as "poor" indicates that a patient is likely developing emerging tumor resistance to these classes of drugs.

Results

Classification labels produced by the classifier for patient serum samples at all available time points are shown in FIG. 1. Serum samples that were classified as "good" are drawn as triangles, samples that were classified as "poor" are labeled as diamonds, and samples for which the classifier returned a result of "undefined" are labeled as solid squares. The patients are ordered vertically along the Y axis by their baseline label, with the 33 patients with a baseline "poor" grouped at the bottom, the 76 patients with a baseline "good" grouped above them, and the two baseline "undefined" patients located at the top of the Y axis. The class labels for a given patient, and changes they exhibit over time, can be observed in FIG. 1 by reading horizontally from a given point on the Y axis across the Figure from left to right. For example, the sequence of symbols 100A, 100B and 100C denote the class labels assigned to three different patients at times measured along the X (time) axis.

FIG. 1 also shows by the white square symbol the progression times (time to progression, TTP).

FIG. 1 shows that in the vast majority of cases that patients that exhibit a "good" label at baseline remained "good" until progression (TTP), and those that exhibited a "poor" at baseline remained poor overall. There is also a visible change of "good" patients to "poor" or "undefined" which is correlated with the time of progression. These changes are summarized in Table 2.

TABLE 2

A summary of changes of classification label for serum samples from "good" (at baseline) to "poor" or undefined at progression.

| | Total n. | At disease progression | | |
|---|---|---|---|---|
| Baseline | 111 | Veristrat+ | Veristrat− | Undefined |
| VeriStrat + (good) | 76 (68%) | 48 (64%) | 22 (29%) | 5 |
| VeriStrat − (poor) | 33 (30%) | 4 (13%) | 28 (87%) | 1 |
| Undefined | 2 (2%) | 2 | 0 | 0 |

Note:
data was missing for one patient at disease progression.

A statistical analysis using a chi-squared test showed that these changes are statistically significant with a p-value of 0.01 (using the null-hypothesis that these changes arise by chance).

Figure 2:
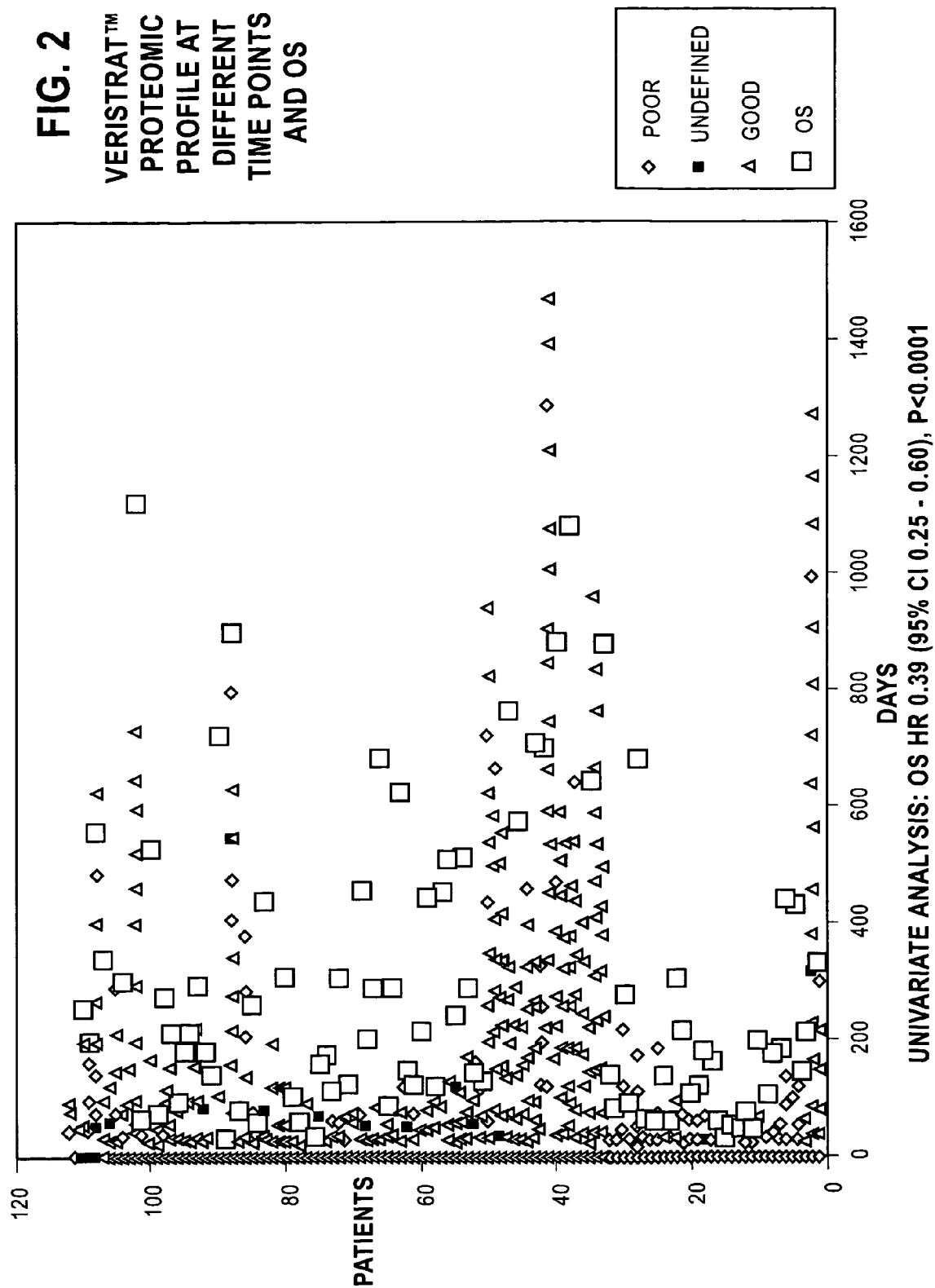
FIG. 2 is a graph plotting the changes in classification labels for 111 patients (arranged along the vertical axis) at different times, with time plotted in days along the horizontal axis. The overall survival ("OS") for each of the patients is indicated by the square symbol.

FIG. 2 is a graph plotting class labels for serum samples of all patients and all time points together with the measured overall survival (OS). Serum samples that produced a class label "good" are drawn as triangles, those that were classified as poor are drawn as diamonds, and those that were classified as "undefined" are drawn in as solid squares. The patients are ordered in the vertical axis by their baseline class label. Class labels for a given patient over time are observed by reading across the graph to the right. The univariate analysis confirms that the baseline "good" and baseline "poor" labels provide statistically significant separation of Kaplan-Meier survival curves for the "good at baseline" and "poor at baseline" groups, that was previously observed.

To further elucidate which patients are changing from "good" to "poor" at progression we performed a subgroup analysis, which is summarized in TABLES 3A-3F below. It turns out that the group of patients that is most likely to change from "good" to "poor" or "undefined" is the group of male (ex)smokers. Female non-smokers rarely change their class label during gefitinib treatment. If we assign a change in the classification label from good to poor/undefined as indicative of emerging tumor resistance to EGFR-Is (as supported by the observed correlation to progression, i.e. the drugs are no longer effective for tumor control), then VeriStrat constitutes the first molecular diagnostics of drug efficacy during treatment.

This finding is interesting as it is well understood that population factors like gender and smoking status are general prognostic markers for NSCLC patients. One could tentatively conclude that the reason that female non-smokers do well overall, and are good candidates for EGFR-I treatment, because they do not develop resistance to EGFR-Is as the group of male and (ex) smokers.

TABLE 3A

Subgroup Table for class label changes at progression for the subgroup of (ex)smokers. The changes are significant with a p-value of 0.0008.

| | Good | Poor | Undefined |
|---|---|---|---|
| Baseline | 61 | 28 | 1 |
| Progression | 36 | 46 | 6 |

TABLE 3B

Subgroup Table for class label changes at progression for the subgroup of adenocarcinoma patients. The changes are on the borderline of significance with a p-value of 0.084.

|  | Good | Poor | Undefined |
|---|---|---|---|
| Baseline | 42 | 12 | 1 |
| Progression | 30 | 20 | 3 |

TABLE 3C

Subgroup Table for class label changes at progression for the subgroup of Squamous cell carcinoma patients. The changes are on the borderline of significance with a p-value of 0.1.

|  | Good | Poor | Undefined |
|---|---|---|---|
| Baseline | 15 | 10 | 0 |
| Progression | 8 | 16 | 1 |

TABLE 3D

Subgroup Table for class label changes at progression for the subgroup of male patients. The changes are significant with a p-value of 0.0007.

|  | Good | Poor | Undefined |
|---|---|---|---|
| Baseline | 57 | 27 | 0 |
| Progression | 35 | 42 | 1 |

TABLE 3E

Subgroup Table for class label changes at progression for the subgroup of patients who never smoked. The changes are insignificant with a p-value of 0.6.

|  | Good | Poor | Undefined |
|---|---|---|---|
| Baseline | 13 | 3 | 1 |
| Progression | 14 | 3 | 0 |

TABLE 3F

Subgroup Table for class label changes at progression for the subgroup of female patients. The changes are insignificant with a p-value of 0.2.

|  | Good | Poor | Undefined |
|---|---|---|---|
| Baseline | 18 | 5 | 2 |
| Progression | 16 | 9 | 0 |

In summary, the results presented in this disclosure confirm several things:

1) That the class label initially assigned to a patient tends to remain reasonably stable over time.

2). At disease progression, about 30% of the patients whose baseline class label was "good" switch to a "poor" (or undefined) profiles. These changes are statistically significant.

3) Certain subgroups of patients are more likely to exhibit a change in the class label at progression, especially males and (ex) smokers, i.e. such patients become resistant to treatment with EGFR pathway targeting drugs.

4) Intra-individual class label changes rarely occur during treatment before progression. Thus, the use of the classification methods of this disclosure can be used in treatment efficacy monitoring for NSCLC patients with EGFR pathway targeting drugs.

EXAMPLE

Figure 3:
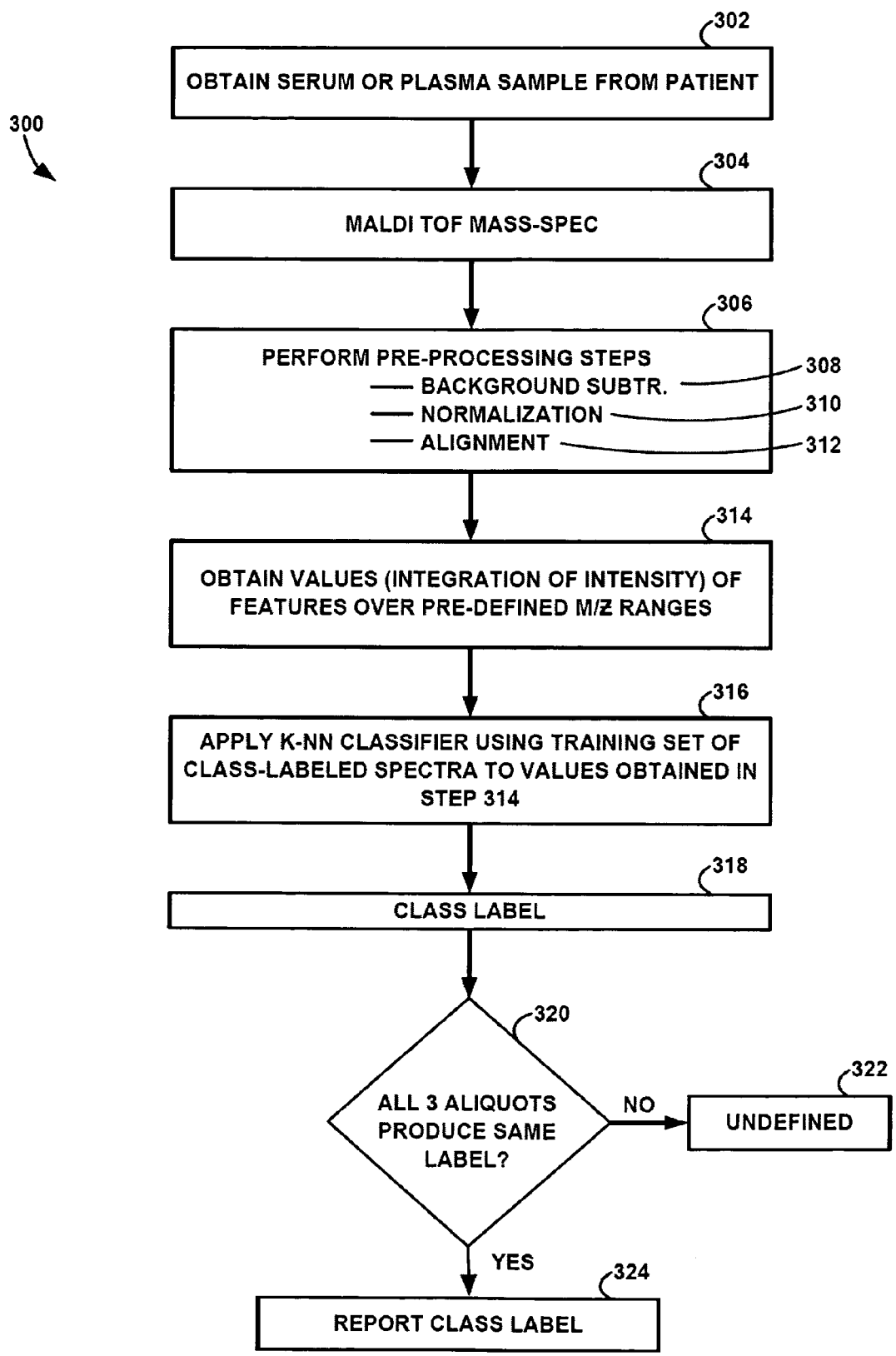
FIG. 3 is a flow chart showing a method for monitoring a patient in accordance with a preferred embodiment of this invention.

Methods for how this invention can be practiced will now be described in further detail. As an initial step, a baseline classification of a plasma or serum sample of the patient using mass spectrometry and classification using a training set is obtained, in the manner described in detail in our prior application published as U.S. 2007/0231921. The methodology is shown in FIG. 3 described below. If the class label for the patient sample is "good", the result indicates that the patient is likely to benefit from a drug targeting the EGFR pathway, such as gefitinib, erlotinib or cetuximab. The patient is then prescribed one of these drugs.

During the course of treatment by administration of an EFGR-I drug, the patient is monitored periodically to determine whether the class label for a serum sample of the patient has changed. A change from "good" to "poor" indicates that the patient may be developing a non-responsiveness to further administration of the EGFR-I drug. This monitoring is illustrated in flow chart form in FIG. 3. The monitoring, shown as process 300, is performed at periodic intervals, such as an interval of between 30 and 100 days.

At step 302, a serum or plasma sample is obtained from the patient. In one embodiment, the serum samples are separated into three aliquots and the mass spectrometry and subsequent steps 304, 306 (including sub-steps 308, 310 and 312), 314, 316 and 318 are performed independently on each of the aliquots.

At step 304, the sample is subject to mass spectrometry. A preferred method of mass spectrometry is MALDI time of flight (TOF) but other methods are possible. Mass spectrometry produces data points that represent intensity values at a multitude of mass/charge (m/z) values, as is conventional in the art. In one example embodiment, the samples are thawed and centrifuged at 1500 rpm for five minutes at four degrees Celsius. Further, the serum samples may be diluted 1:10, or 1:5, in MilliQ water. Diluted samples may be spotted in randomly allocated positions on a MALDI plate in triplicate (i.e., on three different MALDI targets). After 0.75 ul of diluted serum is spotted on a MALDI plate, 0.75 ul of 35 mg/ml sinapinic acid (in 50% acetonitrile and 0.1% trifluoroacetic acid (TFA)) may be added and mixed by pipetting up and down five times. Plates may be allowed to dry at room temperature. It should be understood that other techniques and procedures may be utilized for preparing and processing serum in accordance with the principles of the present invention.

Mass spectra may be acquired for positive ions in linear mode using a Voyager DE-PRO or DE-STR MALDI TOF mass spectrometer with automated or manual collection of the spectra. Seventy five or one hundred spectra are collected from seven or five positions within each MALDI spot in order to generate an average of 525 or 500 spectra for each serum specimen. Spectra are externally calibrated using a mixture of protein standards (Insulin (bovine), thioredoxin (*E. coli*), and Apomyglobin (equine)).

At step 306, the spectra obtained in step 304 are subject to one or more pre-defined pre-processing steps. The pre-processing steps 306 are implemented in a general purpose computer using software instructions that operate on the mass spectral data obtained in step 304. The pre-processing steps 306 include background subtraction (step 308), normalization (step 310) and alignment (step 312). The step of background subtraction preferably involves generating a robust, asymmetrical estimate of background in the spectrum and subtracts the background from the spectrum. Step 308 uses the techniques described in U.S. 2007/0231921 and U.S.

2005/0267689, which is incorporated by reference herein. The normalization step 310 involves a normalization of the background subtracted spectrum. The normalization can take the form of a partial ion current normalization, or a total ion current normalization, as described in our prior patent application U.S. 2007/0231921. Step 312 aligns the normalized, background subtracted spectrum to a predefined mass scale, as described in U.S. 2007/0231921, which can be obtained from investigation of the training set used by the classifier.

Once the pre-processing steps 306 are performed, the process 300 proceeds to step 314 of obtaining integrated intensity values of selected features (peaks) in the spectrum over pre-defined m/z ranges. Using the peak-width settings of a peak finding algorithm, the normalized and background subtracted amplitudes may be integrated over these m/z ranges and assigned this integrated value (i.e., the area under the curve between the width of the feature) to a feature. For spectra where no peak has been detected within this m/z range, the integration range may be defined as the interval around the average m/z position of this feature with a width corresponding to the peak width at the current m/z position.

At step 314, as described in our patent application published as US 2007/0231921, the integrated intensity values of features in the spectrum is obtained at one or more of the following m/z ranges:
5732 to 5795
5811 to 5875
6398 to 6469
11376 to 11515
11459 to 11599
11614 to 11756
11687 to 11831
11830 to 11976
12375 to 12529
23183 to 23525
23279 to 23622 and
65902 to 67502.

In a preferred embodiment, values are obtained at least eight of these m/z ranges, and more preferably at all 12 of these ranges. The significance, and methods of discovery of these peaks, is explained in the prior patent application publication U.S. 2007/0231921. It has been discovered that this set of peaks is not only useful for patient selection and monitoring of NSCLC patients, but also CRC patients and HNSCC cancer patients as well.

At step 316, the values obtained at step 314 are supplied to a classifier, which in the illustrated embodiment is a K-nearest neighbor (KNN) classifier. The classifier makes use of a training set of class labeled spectra from other patients. The application of the KNN classification algorithm to the values at 314 and the training set is explained in our patent application publication U.S. 2007/0231921. Other classifiers can be used, including a probabilistic KNN classifier or other classifier.

At step 318, the classifier produces a label for the spectrum, either "good", "poor" or "undefined". As mentioned above, steps 304-318 are performed in parallel on three separate aliquots from a given patient sample. At step 320, a check is made to determine whether all three aliquots produce the same class label. If not, an undefined result is returned as indicated at step 322. If all aliquots produce the same label, the label is reported as indicated at step 324.

If the label reported at step 324 is "good" it indicates that the patient is likely to benefit from continued administration of the EGFR pathway targeting drug. If the label reported at step 324 is "poor" it indicates that the patient is likely developing a resistance or non-responsiveness to treatment by such a drug.

It will be understood that steps 306, 314, 316 and 3118 are typically performed in a programmed general purpose computer using software coding the pre-processing step 306, the obtaining of integrated intensity values in step 314, the application of the KNN classification algorithm in step 316 and the generation of the class label in step 318. The training set of class labeled spectra used in step 316 is stored in memory in the computer or in a memory accessible to the computer.

From the foregoing, it will be appreciated that we have disclosed a method of determining whether a NSCLC, HNSCC or CRC patient has developed non-responsiveness to treatment with a drug targeting the EGFR pathway, comprising the steps of:

a) obtaining a mass spectrum from a blood-based sample from the patient;

b) performing one or more predefined pre-processing steps on the mass spectrum obtained in step a)(e.g., background subtraction, normalization and spectral alignment);

c) obtaining integrated intensity values of selected features in said spectrum at one or more predefined m/z ranges after the pre-processing steps on the mass spectrum in step b) have been performed;

d) using the values obtained in step c) in a classification algorithm using a training set comprising class-labeled spectra produced from blood-based samples from other patients to identify the patient as having developed a non-responsiveness to treatment with the said drug.

Examples of the drug include gefitinib, erlotinib, or cetuximab or equivalent thereof (e.g., generic version or other drug which would be considered equivalent to these drugs).

Steps a)-d) are preferably performed periodically. For example they are performed at intervals of between 30 and 100 days.

In another aspect, a method is disclosed of facilitating treatment of a NSCLC, HNSCC or CRC patient, comprising the steps of:

1) assigning a baseline class label for the patient using a classifier operating on integrated intensity values at pre-defined m/z ranges in mass-spectral data obtained from a blood-based sample of the patient and a training set comprising class-labeled spectra from other patients, the baseline class label indicating whether the patient is likely to benefit from administration of a drug targeting an epidermal growth factor receptor pathway. If the baseline class label is "good" (or the equivalent), the patient would be likely to benefit and the drug is administered to the patient; and 2) thereafter, while the patient is being treated with the drug, a) obtaining a mass spectrum of a blood-based sample of the patient, b) performing one or more predefined pre-processing steps on the mass spectrum, c) obtaining integrated intensity values of selected features in said spectrum at one or more predefined m/z ranges after the pre-processing steps on the mass spectrum have been performed, and d) assigning a further class label for the sample using the classifier and the training set, the further class label indicating whether the patient has developed a non-responsiveness to the treatment with the said drug. This step 2) is preferably performed periodically over the course of treatment, e.g., every 30, 60 or 100 days.

Variations from the particular details of the preferred embodiments disclosed are of course possible without departure from the scope of the invention. All questions of scope are to be determined by reference to the appended claims. The appended claims are further considered part of the present inventive disclosure.

What is claimed is:

1. A method of facilitating treatment of a non-small cell lung cancer (NSCLC) comprising the steps of:
   1) assigning a baseline class label for the patient using a classifier operating on integrated intensity values at predefined m/z ranges in mass-spectral data obtained from a blood-based sample of the patient and a training set comprising class-labeled spectra from other patients, the baseline class label indicating whether the patient is likely to benefit from administration of a drug targeting an epidermal growth factor receptor pathway, wherein if the baseline class label is "good" (or the equivalent), the drug is administered to the patient; and
   2) thereafter, while the patient is being treated with the drug, a) obtaining a mass spectrum of a blood-based sample of the patient, b) performing one or more predefined pre-processing steps on the mass spectrum, c) obtaining integrated intensity values of selected features in said spectrum at said one or more predefined m/z ranges after the pre-processing steps on the mass spectrum have been performed, and d) assigning a further class label for the sample using the classifier and the training set, the further class label indicating whether the patient has developed a non-responsiveness to the treatment with the said drug wherein the drug is selected from the group of drugs consisting of gefitinib or equivalent thereof; erlotinib or equivalent thereof and cetuximab or equivalent thereof.

2. The method of claim 1, wherein the patient is a male smoker or male ex-smoker.

3. The method of claim 1, wherein step 2) including sub-steps a)-d) are performed periodically during the course of treatment of the patient.

* * * * *